United States Patent
Steele et al.

(10) Patent No.: US 8,591,519 B2
(45) Date of Patent: Nov. 26, 2013

(54) SURGICAL INSTRUMENT WITH CYCLOIDAL GEAR SYSTEM

(75) Inventors: Bradley E. Steele, Germantown, TN (US); Thomas V. McGahan, Memphis, TN (US); Jacob R. Zimmerman, North Little Rock, AR (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 484 days.

(21) Appl. No.: 12/915,947

(22) Filed: Oct. 29, 2010

(65) Prior Publication Data

US 2012/0109126 A1    May 3, 2012

(51) Int. Cl.
  *A61B 17/88*  (2006.01)
  *A61B 17/90*  (2006.01)
(52) U.S. Cl.
  USPC ............ 606/104; 227/141; 475/162; 475/168
(58) Field of Classification Search
  USPC .............. 606/75, 86 A, 86 B, 86 R, 104, 301; 173/216; 227/175.1–182.1, 141–156; 475/162–164, 168, 170, 173, 176
  See application file for complete search history.

(56) References Cited

U.S. PATENT DOCUMENTS

| | | |
|---|---|---|
| 3,797,497 A | 3/1974 | Crim et al. |
| 5,226,906 A | 7/1993 | Crombie et al. |
| 5,863,272 A | 1/1999 | Anderson |
| 5,993,454 A | 11/1999 | Longo |
| 6,279,714 B1 * | 8/2001 | Hsu .......................... 192/223.2 |
| 6,312,441 B1 | 11/2001 | Deng |
| 6,663,641 B1 | 12/2003 | Kovac et al. |
| 6,675,911 B2 | 1/2004 | Drissen |
| 6,824,495 B1 | 11/2004 | Krischner |
| 6,866,607 B2 | 3/2005 | Nishiji et al. |
| 6,958,071 B2 | 10/2005 | Carusillo et al. |
| 7,021,399 B2 | 4/2006 | Driessen |
| 2006/0265006 A1 | 11/2006 | White et al. |
| 2007/0270859 A1 | 11/2007 | Companioni et al. |
| 2008/0243123 A1 | 10/2008 | Gordis Wallis et al. |
| 2009/0090764 A1 | 4/2009 | Viola |
| 2009/0270880 A1 | 10/2009 | Gale et al. |
| 2010/0076461 A1 | 3/2010 | Viola et al. |

* cited by examiner

Primary Examiner — Matthew Lawson

(57) ABSTRACT

A surgical instrument for applying a rotational force to a structural element during a surgical procedure. The instrument may be designed for increasing an input force to produce an enlarged output force adequate for fracturing an excess section of the elongated element from a remainder of the structural element. The instrument may include an input mechanism that receives an external rotational input force, a cycloidal gear system that multiples the input force, and an output mechanism that attaches to and delivers the multiplied rotational output force to the excess section of the structural element. The output mechanism may also be configured to capture the separated excess section. The instrument may include a housing and a handle for grasping and manipulating during the surgical procedure.

20 Claims, 10 Drawing Sheets

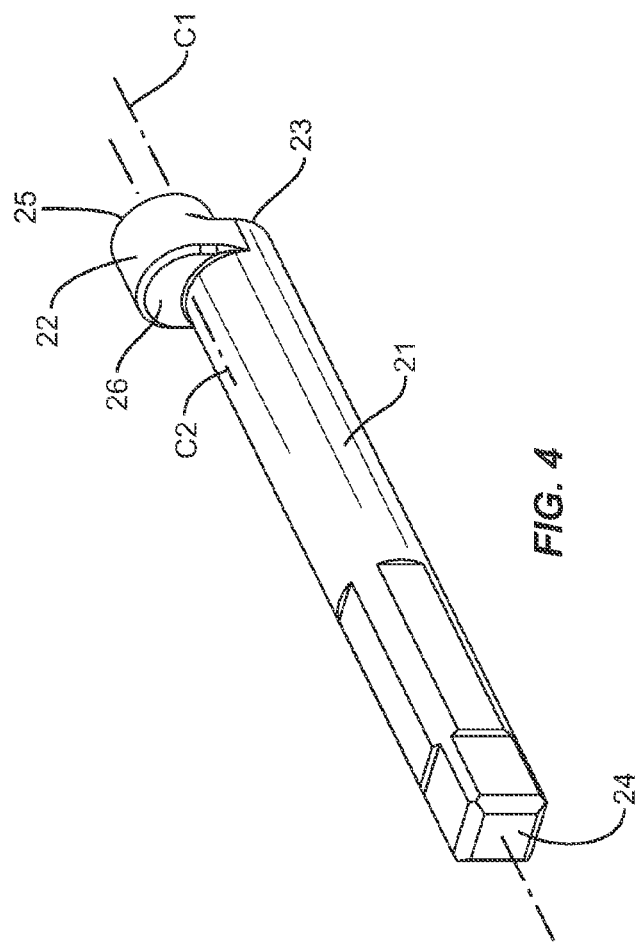
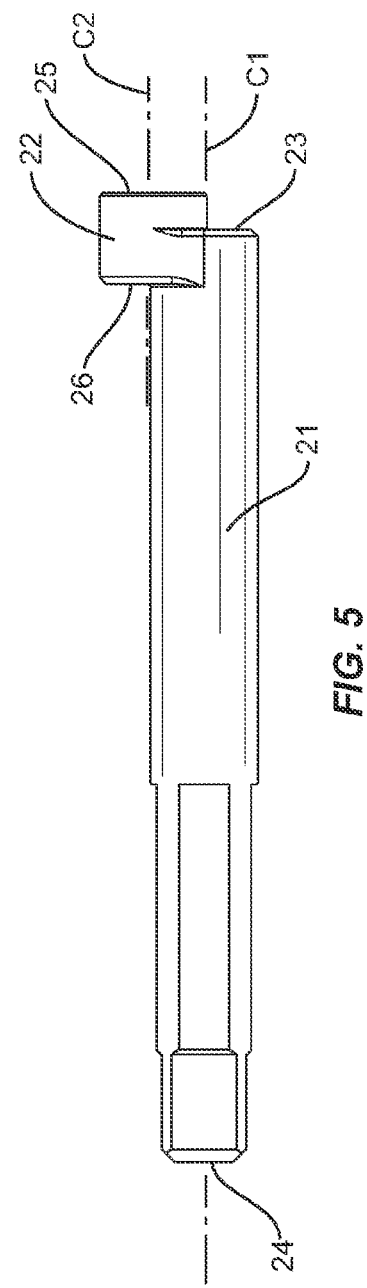

SURGICAL INSTRUMENT WITH CYCLOIDAL GEAR SYSTEM

BACKGROUND

The present application is directed to surgical instruments for applying a rotational force to an element and, more particularly, to a surgical instrument with a cycloidal gear system.

Various types of structural elements are used in patients during surgical procedures. Examples include but are not limited to rods such as for attaching to vertebral members or to a broken femur, bone anchors for attaching an elongated element to a bone, pins for attaching together bones or bone sections, and posts for attaching to bones and/or tissue. It is often necessary to remove sections of the structural elements, such as a head of a set screw or an excess length of a rod. Many times the removal occurs after the structural element have been inserted into a patient. Various instruments are presently used for removing the excess sections. However, the instruments have various drawbacks that add complexity to the surgical procedure.

Some of the previous instruments have a relatively large size. The large size is necessary to generate an adequate force to remove the excess section from the remainder of the structural member. One example is an instrument with large lever arms. The large lever arms are necessary for the instrument to create an adequate shearing force, but the large sizes make the instruments difficult to use in small surgical sites. Further, the instruments may be too large to reach the needed area within the surgical site where the section is to be removed from the remainder of the structural member.

Other instruments are uncontrollable at the time the section is removed. This is caused by the relatively large force necessary to remove the section and the release of the force at the moment of removal. The force release may cause the instruments to "jump" or "buck" making it difficult to control for the medical practitioner, and may cause a shock to the patient.

SUMMARY

The present application is directed to surgical instruments for applying a rotational force to a structural element. The surgical instrument may include a housing, an input mechanism, and an output mechanism that are each aligned along a longitudinal axis. The input mechanism may include an eccentric shaft with a first section that extends axially on the longitudinal axis and a second section that is radially offset from the longitudinal axis. The input mechanism may be rotatable relative to the housing. The output shaft may extend axially on the longitudinal axis and may include a receptacle configured to engage with the element. The output shaft may be rotatable relative to the housing. The instrument may also include a cycloidal gear system with first and second annular members that are axially spaced along the longitudinal axis. Each of the annular members may have an opening aligned on the longitudinal axis and teeth that radially extend inward toward a center of the opening. The first annular member may have a different number of teeth than the second annular member. The cycloidal gear system may also include first and second gears that are axially spaced along the longitudinal axis with the first gear aligned to engage with the first annular member and the second gear aligned to engage with the second annular member. Each of the gears may have teeth that radially extend outward away from the longitudinal axis and engage with the teeth on the respective annular members. The gears may be connected to the second section of the eccentric shaft. The first gear may have a different number of teeth than the second gear. One of the annular members may be non-rotatably attached to the housing and the other of the annular members may be rotatably attached to the housing.

The surgical instrument may also include a drive shaft with a first axial section that extends axially on a longitudinal axis and a second axial section positioned at a distal end of the first axial section and may be radially offset from the longitudinal axis. A drive member may be positioned distally from the drive shaft and may include a proximal side that faces towards the drive shaft and an opposing distal side. The distal side may include fingers that extend axially along the longitudinal axis and are radially spaced outward from the longitudinal axis. A first annular member may have a central opening that extends around the longitudinal axis and teeth that face radially inward towards the longitudinal axis. A first gear may be attached to the second axial section of the drive shaft and may have teeth that extend radially outward away from the longitudinal axis to engage with the teeth of the first annular member. A second annular member may be aligned along the longitudinal axis with the first annular member. The second annular member may have a central opening that extends around the longitudinal axis and teeth that face radially inward towards the longitudinal axis. The first annular member may be attached to the first side of the drive member. The second annular member may include a different number of teeth than the first annular member. A second gear may be attached to the first gear and may have teeth that extend radially outward away from the longitudinal axis to engage with the teeth of the second annular member. An elongated output member may have a first end that engages with the drive member and a second end with a mount configured to engage with the element.

The surgical instrument may also include an input shaft with a first section that extends axially on the longitudinal axis and a second section radially offset from the longitudinal axis. An output shaft may extend axially on the longitudinal axis and may include a receptacle configured to engage with the element. First and second annular members may be aligned along the longitudinal axis. Each of the annular members may have a center opening centered on the longitudinal axis and teeth that radially extend inward toward the longitudinal axis. The first annular member may have a different number of teeth than the second annular member. First and second gears may be operatively connected to the second section of the input shaft with the first gear aligned with the first annular member to engage with the first annular member and the second gear aligned with the second annular member to engage with the second annular member.

The various aspects of the various embodiments may be used alone or in any combination, as is desired.

BRIEF DESCRIPTION OF THE DRAWINGS

FIG. 4 is a perspective view of an eccentric shaft drive gear.
FIG. 5 is a side view of an eccentric shaft drive gear.

DETAILED DESCRIPTION

Figure 1:
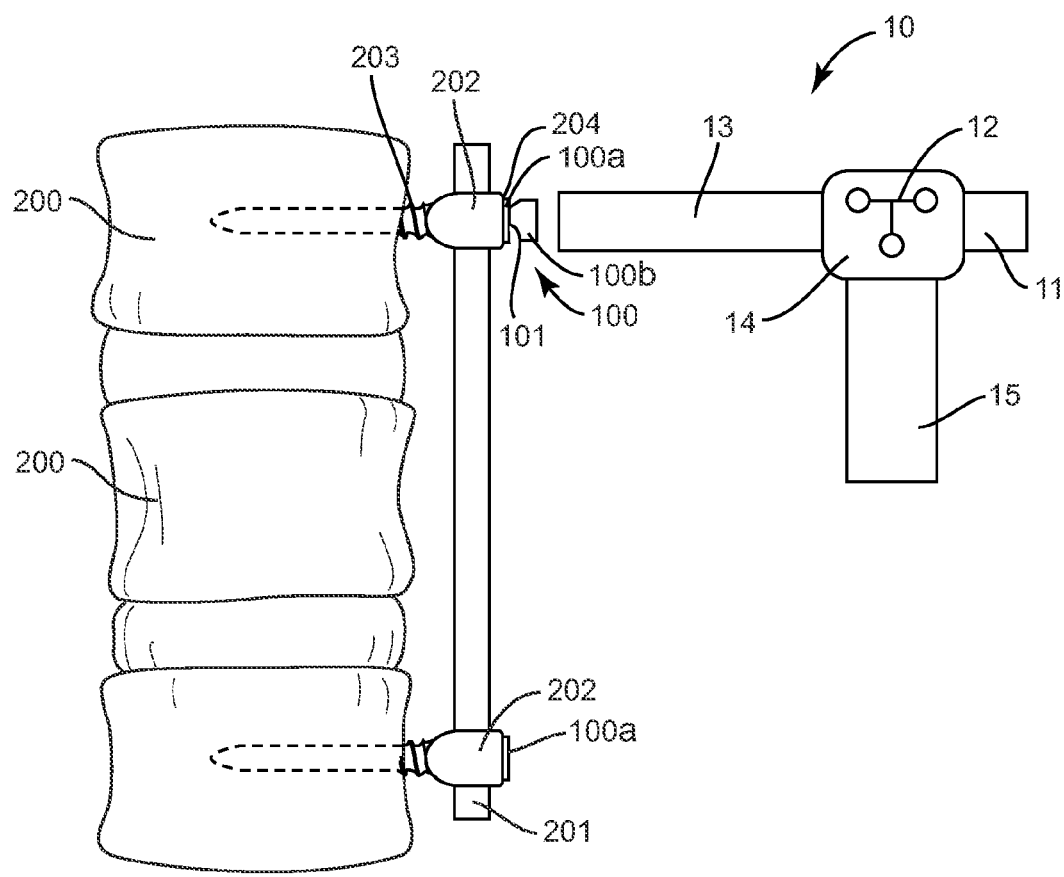
FIG. 1 is a schematic view of an instrument and a fastener attached to bone.

The present application is directed to a surgical instrument for applying a rotational force to a structural element during a surgical procedure. The instrument is designed for increasing an input force to produce an enlarged output force. The enlarged output force is adequate for fracturing an excess section of the elongated element from a remainder of the structural element. As schematically illustrated in FIG. 1, the instrument 10 generally includes an input mechanism 11 that receives an external rotational input force, a cycloidal gear system 12 that multiples the input force, and an output mechanism 13 that attaches to and delivers the multiplied rotational output force to the excess section of the structural element 100. The applied output force causes an excess section 100b of the structural element 100 to fracture from a section 100a that remains in the patient. The output mechanism 13 may also be configured to capture the separated excess section 100b. The instrument 10 may include an exterior housing 14 with a handle 15 for grasping and manipulating during the surgical procedure.

One example of a structural element 100 acted upon by the instrument 10 is a set screw as illustrated in FIG. 1. The set screw includes a first section 100a that seats within a head 204 of an anchor 202 to capture an elongated element 201 and a second section 100b. The second section 100b is necessary for initially positioning and/or initially attaching the first section 100a to the anchor 202. Afterwards, the second section 100b is superfluous and can be removed from the first section 100a. The anchor 202 that receives the set screw also includes a shaft 203 attached to a bone 200.

Figure 2:
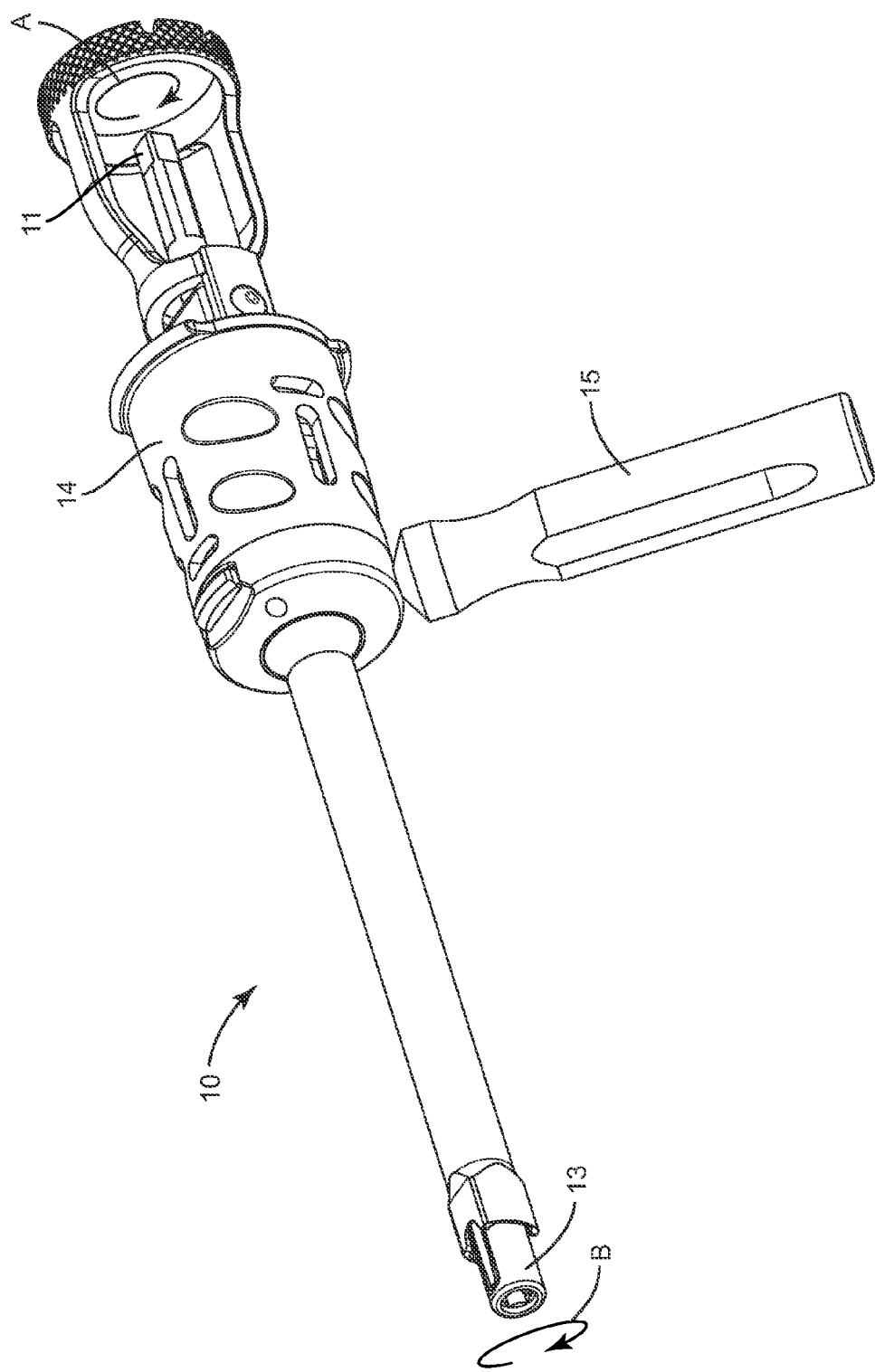
FIG. 2 is a perspective view of an instrument.

FIG. 2 illustrates an exterior view of an instrument 10. The instrument 10 includes the input mechanism 11 that extends outward from a first side of a housing 14, and an output mechanism 13 that extends outward from an opposing second side of the housing 14. The cycloidal gear system (not illustrated in FIG. 2) is housed within an interior of the housing 14 and operatively connects with the input and output mechanisms 11, 13. The handle 15 may also be located to facilitate use during the surgical procedure. The instrument 10 is configured for rotation A of the input mechanism 11 in a first rotational direction resulting in rotation B of the output mechanism 13 in the same rotational direction.

Figure 3:
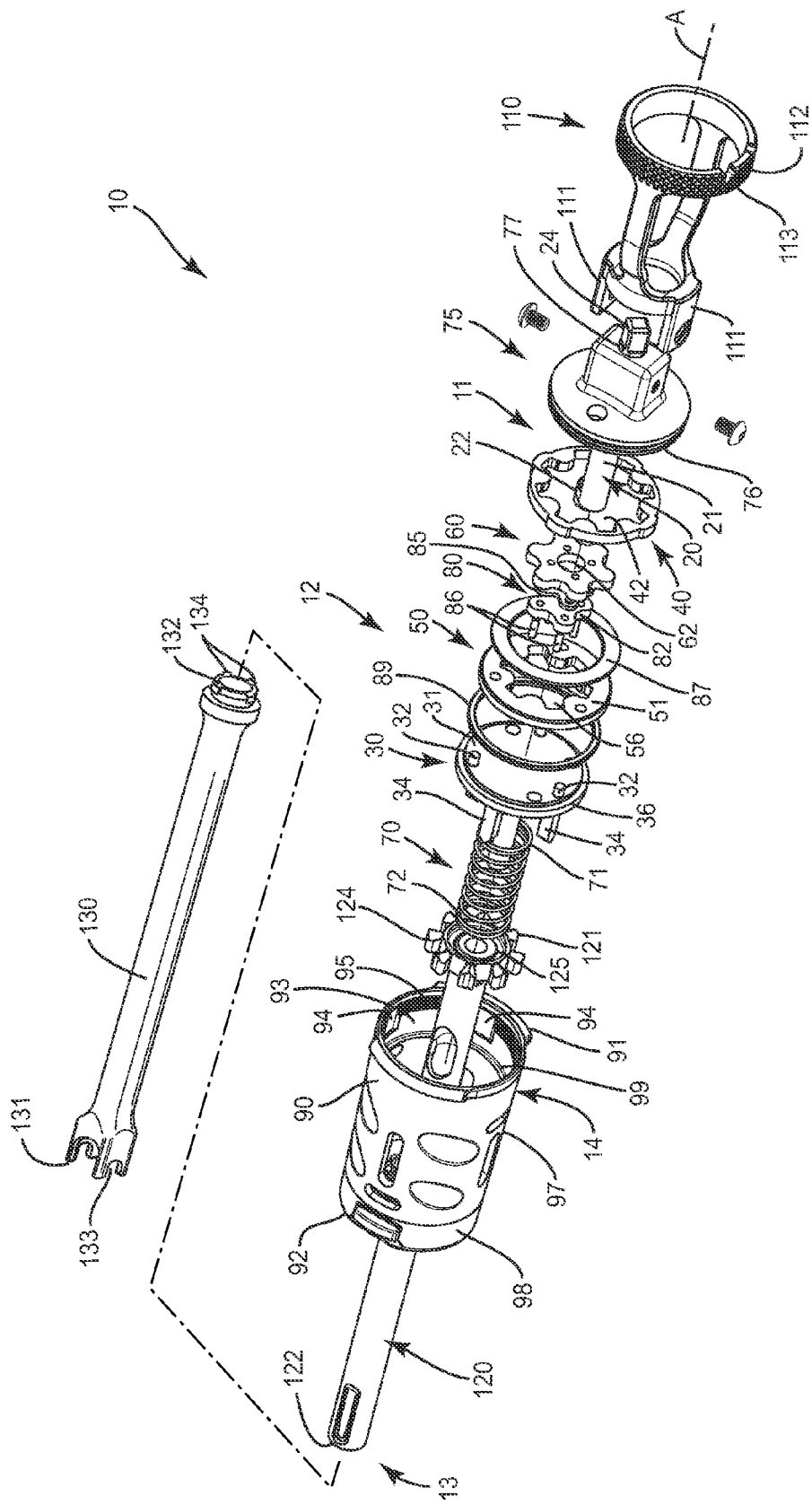
FIG. 3 is an exploded perspective view of an instrument.

FIG. 3 illustrates an exploded view of an instrument 10 that includes the input mechanism 11, the cycloidal gear system 12, and the output mechanism 13. These elements 11, 12, 13 have a relatively small overall size that facilitates use of the instrument 10 in a surgical setting where it is often necessary to work in a reduced space. The instrument 10 includes an elongated shape with a longitudinal axis A extending through each of the elements 11, 12, 13.

The input mechanism 11 includes an eccentric shaft drive gear 20 positioned at a proximal end of the instrument 10 as illustrated in FIGS. 3, 4 and 5. The drive gears 20 include an elongated shape with a first section 21 that extends between distal and proximal ends 23, 24, and a second section 22 that extends between its own distal and proximal ends 25, 26. The sections 21, 22 are eccentrically positioned with a longitudinal axis C1 of the first section 21 radially offset from a longitudinal axis C2 of the second section 22. The drive gear 20 is positioned in the instrument 10 with the longitudinal axis C1 co-axial with the longitudinal axis A of the instrument 10. This positions the longitudinal axis C2 of the second section 22 radially outward from the longitudinal axis A of the instrument 10.

The second section 22 is also positioned axially outward from the first section 21 with the distal end 25 of the second section 22 located axially beyond the distal end 23 of the first section 21. The second section 22 is configured to engage with a gear 60. In one embodiment, the second section has a circular cross-sectional shape.

The proximal end 24 of the first section 21 is configured to engage with an external drive force. The proximal end 21 may include a polygonal cross-sectional shape with a number of flat sides. The flat sides are configured to facilitate receipt of the external input force. The proximal end 24 extends outward beyond the housing 14 (FIG. 2) and is accessible for attachment with the external input force. The length of the drive gear 20 (including both sections 21, 22) may vary depending upon the instrument 10. In one embodiment, the length is about 2.25 inches. In another embodiment, the length is about 3.00 inches.

Figure 6:
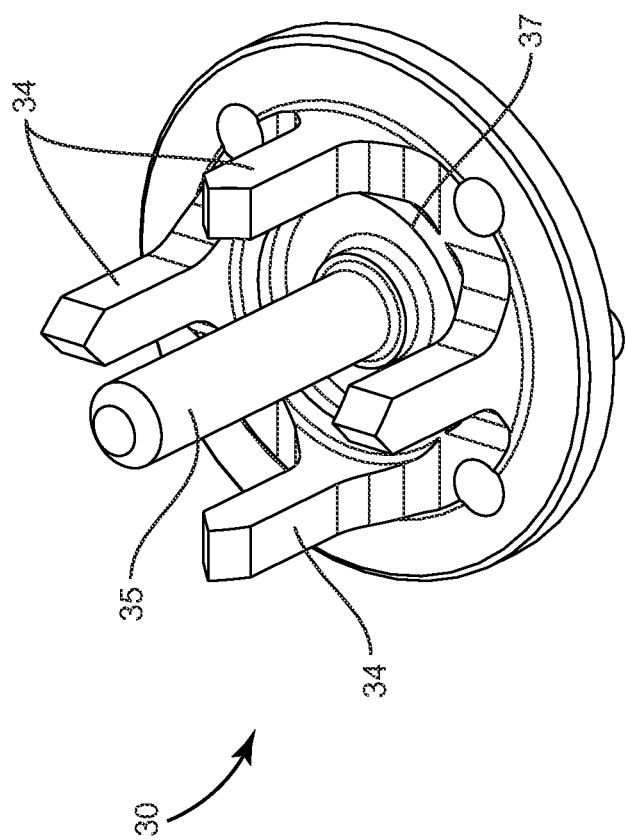
FIG. 6 is a perspective view of a distal end of a drive plate.

A drive plate 30 is positioned distally from the distal end 22 of the drive gear 20. The drive plate 30 includes a proximal side 31 that faces towards the drive plate 30. FIGS. 3 and 6 include the drive plate 30 having a circular shape and the proximal side 31 being substantially flat. Posts 32 extend axially outward along the longitudinal axis A from the proximal side 31 in a proximal direction towards the drive gear 20. The lengths and cross-sectional shapes of the posts 32. FIG. 3 includes three posts 32, although other embodiments may include more than three posts 32. One embodiment includes two posts 32 extending outward from the side 31. Another embodiment includes five posts 32.

The proximal side 31 may also include a shoulder 36 that extends around the periphery. The shoulder 36 is configured to receive an annular bushing 89 that facilitates rotation of the drive plate 30 within the housing 14. Alternatively, bearings may also be positioned along the shoulder 36 to facilitate rotation.

A distal side 37 of the drive plate 30 faces away from the drive gear 20. As illustrated in FIG. 6, the distal side 37 includes fingers 34 that extend axially outward in a distal direction away from the drive gear 20. The fingers 34 are substantially straight and may include various lengths. The fingers 34 may each include one or more flat sides to engage with a gear 124 on a first shaft 120 of the output mechanism 13 as will be explained below. The fingers 34 may include a tapered shape that narrows to a tip to facilitate engagement with the gear 124. The fingers 34 are evenly spaced apart to correspond to the shape of the gear 124. In one embodiment, the drive plate 30 includes four fingers 34, although other embodiments may include different numbers of fingers 34.

A post 35 extends outward in a distal direction from a center of the distal side 37. The post 35 is positioned within an area formed by the fingers 34. The post 35 may include a greater length than the fingers 34 to extend outward a greater distance from the distal side 37. The post 35 may include a circular cross-sectional shape as illustrated in FIG. 6. The drive plate 30 is located in the instrument 10 with the post 35 positioned on and extending along the longitudinal axis A. The fingers 34 are located radially outward from the longitudinal axis A.

Figure 7:
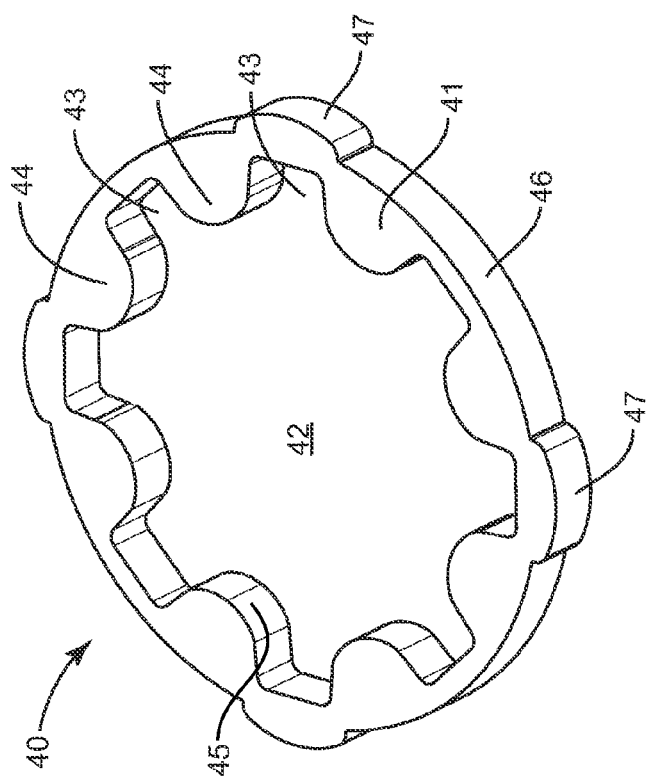
FIG. 7 is a perspective view of a first annular member.

A first annular member 40 is positioned on a proximal side of the drive plate 30 and extends around the drive gear 20. As illustrated in FIGS. 3 and 7, the annular member 40 includes a circular body 41 that extends around a central opening 42. The body 41 includes an interior surface 45 with teeth formed by alternating indents 43 that extend away from a center of the opening 42 and protrusions 44 that extend toward the center. The protrusions 44 include a continuously-curved surface that lead into the indents 43. The indents 43 and protrusions 44 extend completely around the interior surface 45. The number of teeth may vary depending upon the specific torque requirements of the instrument 10. In one embodiment, the first annular member 40 includes eight teeth.

The annular member 40 also includes an exterior surface 46 with one or more tabs 47 that extend radially outward away from the center of the member. The tabs 47 are configured to engage with the housing 14 and prevent rotation between the annular member 40 and the housing 14.

The first annular member 40 is located in the instrument 10 with a center of the opening 42 aligned on the longitudinal axis A. This location places the teeth radially outward from the longitudinal axis A.

Figure 8:
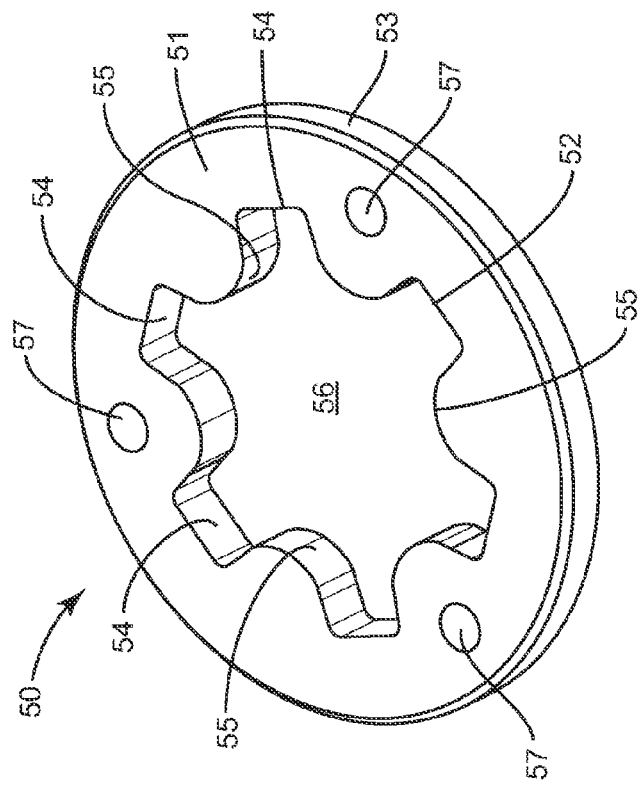
FIG. 8 is a perspective view of a second annular member.

A second annular member 50 is axially offset along the longitudinal axis A and located on distal side of the first annular member 40. As illustrated in FIGS. 3 and 8, the second annular member 50 includes a circular body 51 that extends around a central opening 56. The body 51 includes an interior surface 52 with teeth formed by alternating indents 54 that extend away from a center of the opening 56, and protrusions 55 that extend toward the center. The protrusions 55 include a continuously-curved surface that lead into the indents 54. The indents 54 and protrusions 55 extend completely around the interior surface 52. The number of teeth may vary, with one embodiment including 6 teeth.

The second annular member 50 is located with a center of the opening 56 aligned on the longitudinal axis A of the tool 10. The interior surface 52 of the second annular member 50 is radially closer to the longitudinal axis A than the interior surface 45 of the first annular member 40. In one embodiment, each annular member 40, 50 include the same size outer diameter, with the second annular member 50 including a greater wall thickness between the interior and exterior surfaces 52, 53 than the first annular member 40.

Apertures 57 extend through the second annular member 50 between distal and proximal sides. The apertures 57 are sized and spaced to receive the posts 32 that extend outward from the drive plate 30. This configuration attaches the second annular member 50 to the drive plate 30.

Figure 9:
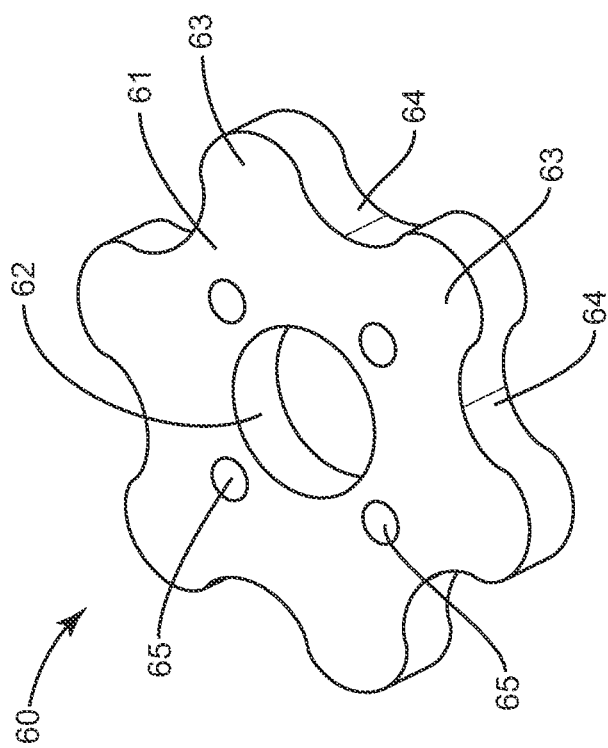
FIG. 9 is a perspective view of a first gear.

A first gear 60 is attached to the distal end 25 of the second section 22 of the drive gear 20. As illustrated in FIGS. 3 and 9, the first gear 60 includes an annular body 61 with an interior opening 62. The opening 62 is positioned within a center of the body 61 and is configured to receive the distal end 25 of the second section 22. The shape of the opening 62 and the cross-sectional shape of the second section 22 may match to facilitate attachment. In this embodiment, each has a circular shape. The periphery of the body 61 includes a number of teeth formed by alternating protrusions 63 and indents 64. The teeth are sized to engage with corresponding teeth on the first annular member 40 during rotation of the first gear 60 as will be explained below. The number of teeth may vary, with one embodiment including six teeth. One or more apertures 65 extend through the body 61 from a distal side to a proximal side.

The first gear 60 is attached to the second section 22 of the drive gear 20. The first gear 60 is also positioned to engage with the first annular member 40. A center of the first gear 60 is radially offset from a center of the annular member 40. Further, the first gear 60 is smaller than the opening 42 of the first annular member 40. Because it is attached to the offset second section 22, the first gear 60 moves around the interior surface 45 of the opening 42 during rotation of the drive shaft 20. The smaller size of the first gear 60 relative to the opening 42 causes the teeth on one side of the first gear 60 to engage with the teeth on the first annular member 40, and for the teeth on the opposing second side of the first gear 60 to be spaced away from nearest teeth. The eccentric shape of the drive shaft 20 causes a center of the first gear 60 to rotate around the longitudinal axis A of the instrument 10.

Figure 10:
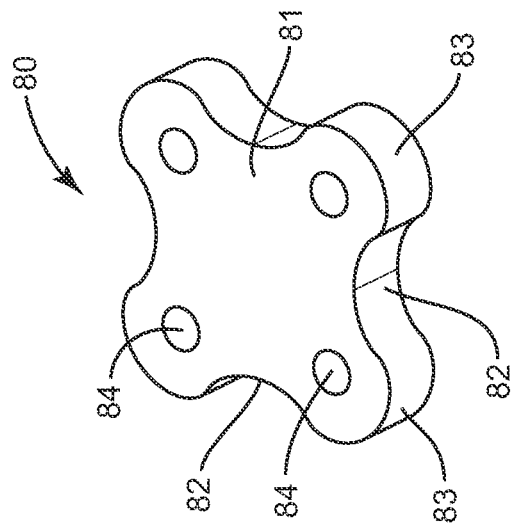
FIG. 10 is a perspective view of a second gear.

A second gear 80 is axially spaced from the first gear 60 and positioned on the distal side of the first gear 60. As illustrated in FIGS. 3 and 10, the second gear 80 includes a body 81 with teeth formed by indents 82 and protrusions 83 that extend around the periphery. The teeth are sized to engage with the corresponding teeth of the second annular member 50. The number of teeth may vary, with one embodiment including four teeth.

One or more apertures 84 extend through the body 81 between a distal side and a proximal side. Theses apertures 84 align with the corresponding apertures 65 in the first gear 60 and receive pins 86 to attach the gears 60, 80 together. The gears 60, 80 may be attached together in additional ways, including but not limited to adhesives and other mechanical fasteners such as a screw.

The second gear 80 is positioned on the distal side of the first gear 60. The second gear 80 is generally smaller than the first gear 60 and fits within the profile of the first gear 60. The teeth of the second gear 80 extend radially outward away from the longitudinal axis A of the tool 10 a lesser distance than the corresponding teeth of the first gear 60.

The second gear 80 is aligned along the longitudinal axis A with the second section 22 of the drive gear 20. The second gear 80 is positioned to engage with the second annular member 50. A center of the second gear 80 is radially offset from a center of the second annular member 50. The second gear 80 is smaller than the opening 56 of the second annular member 50. During rotation of the drive gear 20, the second gear 80 moves around the interior surface 52 of the opening 56. The smaller size of the second gear 80 relative to the opening 56 causes the teeth on one side of the second gear 80 to engage with the teeth on the second annular member 50, and for the teeth on the opposing side of the second gear 80 to be spaced away from nearest teeth. The eccentric shape of the drive shaft 20 causes a center of the second gear 80 to rotate around the longitudinal axis A of the instrument 10. Further, rotation of the second gear 80 causes rotation of the second annular member 50.

A spacer 85 may be positioned between the first and second gears 60, 80. The spacer 85 includes a distal surface that contacts against the second gear 80, and a proximal surface that contacts against the first gear 60. The spacer 85 includes a thickness measured between the surfaces to space the gears 60, 80 axially apart for the first gear 60 to engage with the first annular member 40 and the second gear 80 to engage with the second annular member 50. The spacer 85 has a smaller profile than each of the first and second gears 60, 80 to not interfere with their engagement with the respective annular members 40, 50.

An additional annular spacer 87 may be positioned between the first and second annular members 40, 50. The spacer 87 includes a central opening that extends around the first and second gears 60, 80 as is located around the longitudinal axis A.

A biasing member 70 biases the drive plate 30 away from the first shaft 120 of the output mechanism 13. A proximal end 71 of the biasing member 70 contacts against the distal side 37, and a distal end 72 contacts against a proximal end 121 of the first shaft 120. The biasing member 70 may be a compression spring that maintains the drive plate 30 axially separated from the first shaft 120 when there are no external forces acting on the instrument 10. FIG. 3 illustrates the biasing member 70 being a coil spring with a central channel that extends around the post 35.

The extent to which the cycloidal gear system 12 multiplies the input force depends upon the configuration of the drive gear 20, the first and second annular members 40, 50, and the first and second gears 60, 80. The multiplication may range up to about 80 times the input force. In one embodiment, the cycloidal gear system 12 multiplies the input force by about nine.

The housing 14 extends around the cycloidal gear system 12 and portions of the input mechanism 11 and the output mechanism 13. The housing 14 may form a portion of the exterior of the instrument 10 as illustrated in FIG. 2, or may be an internal housing that is completely or partially covered by another element.

Figure 11:
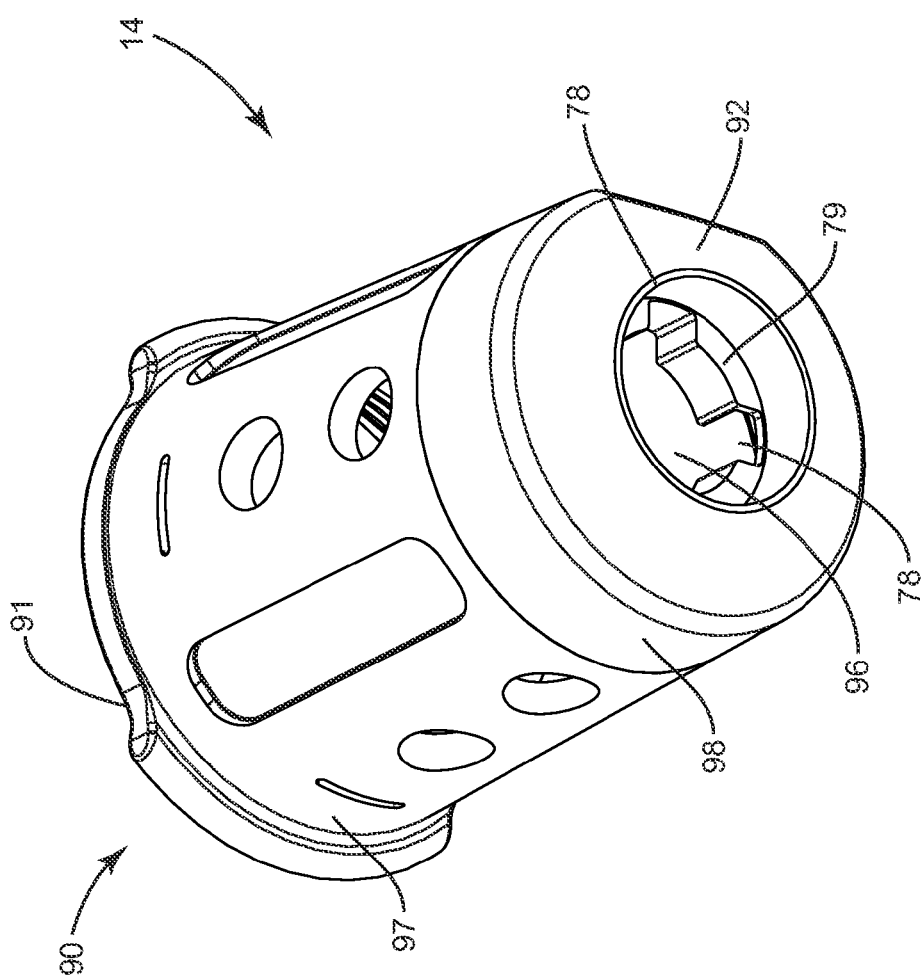
FIG. 11 is a perspective view of a housing.

As illustrated in the embodiments of FIGS. 3 and 11, the housing 14 includes a housing body 90 with an open proximal end 91 and a closed distal end 92. Threads 95 are positioned at the proximal end 91. The distal end 92 includes an opening 96 through which the output mechanism 13 extends. The housing body 90 may be formed from a single piece of material, or may be formed from multiple pieces that are attached together. In one embodiment, the housing body 90 is constructed from a proximal section 97 and a distal section 98.

The housing body 90 includes an open interior 93 that receives the cycloidal gear system 12 and portions of the input and output mechanisms 11, 13. A shelf 99 is positioned axially inward from the proximal end 91 and extends radially inward from the side walls. The shelf 99 forms a seat for contacting against the proximal side 37 of the drive plate 30. The shelf 99 prevents the drive plate 30 from axially moving in a distal direction when a translational force is applied that overpowers the biasing member 70. A second shelf is positioned behind the threads 95 that limit an extent of axial movement of the drive plate 30 in a proximal direction.

Recesses 94 extend radially into the side wall of the housing body 90 at the proximal end 91. The recesses 94 extend axially inward from the proximal end 91 and are spaced axially away from the shelf 99. The recesses 94 are sized and shaped to receive the tabs 47 on the first annular member 40. The shapes and sizes of the proximal end 91 and the first annular member 40 provide for the first annular member 40 to fit within the interior 93 with the tabs 47 extending radially into the recesses 94. This configuration provides for the housing body 90 to fixedly maintain the first annular member 40 (i.e., prevent or reduce the amount of movement of the first annular member 40 within the interior 93).

The recesses 94 may be sized to allow varying amounts of movement of the first annular member 40 relative to the housing body 90. The recesses 94 as illustrated in FIG. 3 are purposefully oversized relative to the tabs 47 for the first annular member 40 to rotate a few degrees relative to the housing body 90 to help meshing of the gear 124 with the fingers 34. Another embodiment features the recesses 94 closely sized relative to the tabs 47 to more rigidly hold the first annular member 40 relative to the housing body 90.

A cap 75 is sized to fit into and close the proximal end 91. The cap 75 includes a circular cross-sectional shape that substantially matches that of the proximal end 91. Threads 76 extend around the circumference and engage with the corresponding threads 95 to attach the cap 75 to the housing body 90. An aperture 77 may extend through a center of the cap 75 to allow for passage of the proximal section of the drive gear 20.

A torque adapter 110 may be attached to the cap 75. The adapter 110 includes a pair of flanges 111 that extend along and attached to opposing sides of the cap 75. A grip 112 may be positioned on the proximal end to facilitate handling and manipulating of the instrument 10. The grip 112 may include an annular shape to extend around the proximal end of the drive gear 20. The adapter 110 may include one of more attachment features 113 to attach to an exterior member (e.g., table, frame) to provide a counter-torque force to the instrument 10 when a rotational force is applied to the drive gear 20. FIG. 3 includes the attachment feature 113 being a cut-out in the grip 112, although the features 113 may include other configurations and may be positioned at other locations along the adapter 110.

A first shaft 120 includes a proximal end 121 and a distal end 122. The distal end 122 includes a receptacle 123 for engaging with the section of the structural member 100 that is to be removed. The proximal end 121 includes a gear 124 with a number of radially-extending projections. The gear 124 is sized to engage with the fingers 34 that extend axially outward from the drive plate 30. The proximal end 121 and/or a surface of the gear 124 form a seat 125 that is contacted by the distal end 72 of the biasing member 70. The seat 125 may include an indent with an axially-extending rim that extends around the circumference that is sized to accommodate the distal end 72 of the biasing member 70.

Figure 13:
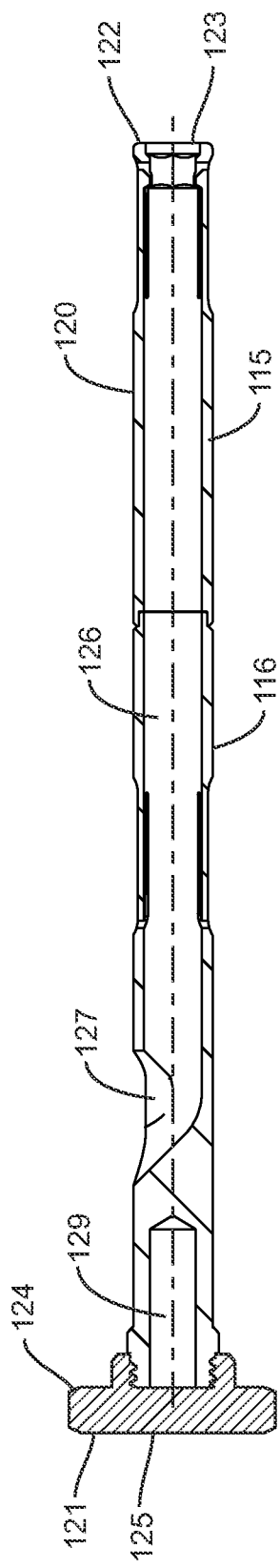
FIG. 13 is a sectional view of the first shaft cut along line XIII-XIII of FIG. 12.

The first shaft 120 also includes an interior bore 126 that receives the excess section of the structural member 100. The receptacle 123 at the distal end 122 forms a portion of the interior bore 126. The receptacle 123 may include flat sides to accommodate the polygonal cross-sectional shapes of the removed sections. The flat sides may extend a limited distance or an entire length of the interior bore 126. An outlet 127 is positioned along the interior bore 126 opposite from the receptacle 123. The outlet 127 provides for removing the removed sections from the first shaft 120. As illustrated in FIG. 13, the proximal end of the interior bore 126 is curved towards the outlet 127 to facilitate removal of the excess sections.

One or more flexible fingers 128 may be positioned along the length of the first shaft 120. The flexible fingers 128 include substantially U-shaped extensions that include an attached distal end and a free proximal end that is cut away from the first shaft 120. The free proximal ends of the fingers 128 may extend a limited distance into the interior bore 126. This configuration allows for the removed sections of the structural members 100 to move proximally through the interior bore 126 towards the outlet 127, but prevents movement in a distal direction where they may inadvertently escape from the distal end 122.

As illustrated in FIG. 13, the proximal end 121 of the first shaft 120 may also include an inlet 129. The inlet 129 is sized to receive the distal section of the post 35 when the first shaft 120 engages with the drive plate 30. FIG. 13 includes the inlet 129 having a back wall and being separated from the interior bore 126.

Figure 12:
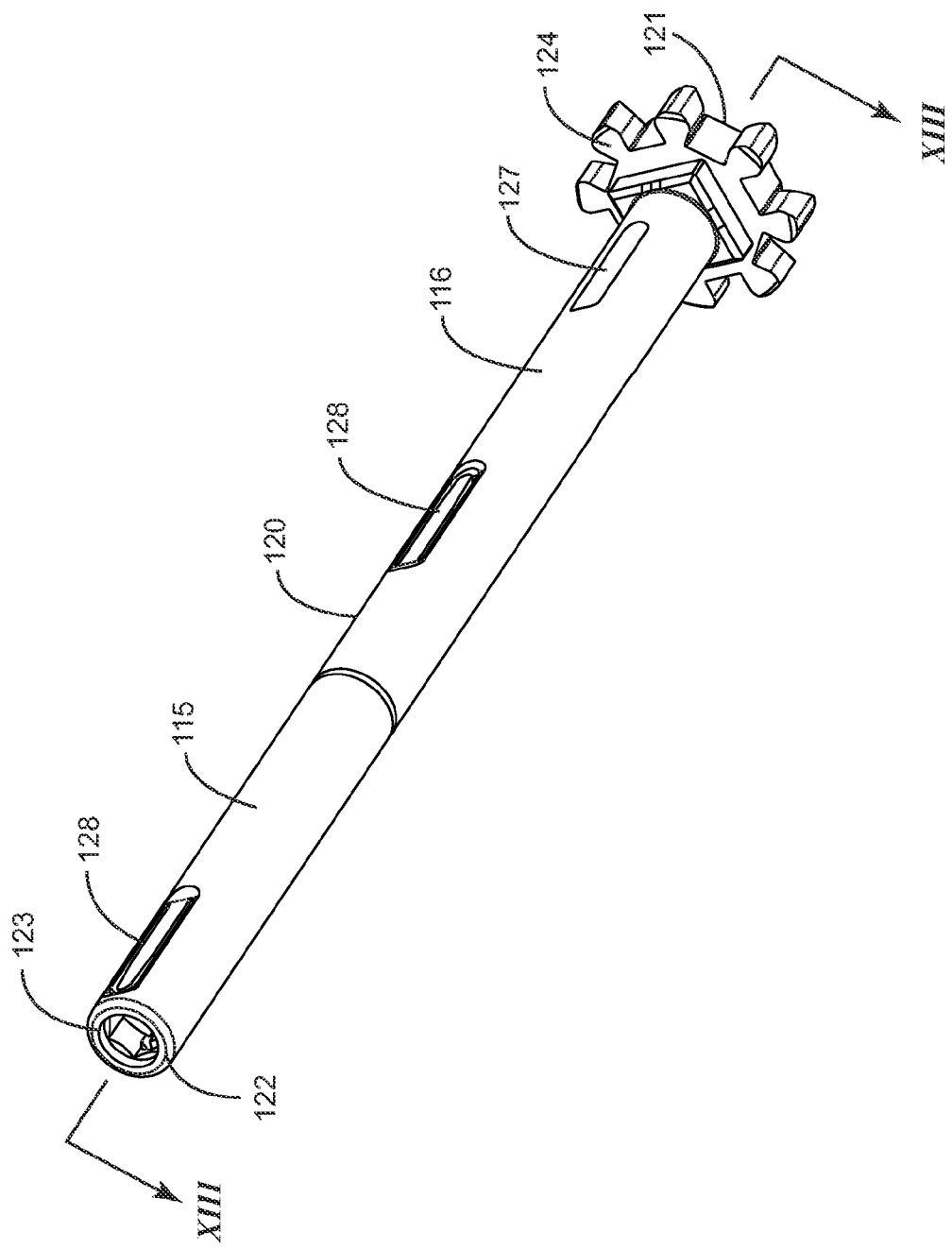
FIG. 12 is a perspective view of a first shaft.

The first shaft 120 may be formed as a single piece, or may include more than one piece. FIGS. 12 and 13 illustrate the first shaft 120 with a distal section 115 and a separate proximal section 116. Further, the gear 124 is a separate piece that is threaded onto the proximal end 121 of the proximal section 116.

The first shaft 120 extends through the opening 96 in the distal end 92 of the housing body 90. The first shaft 120 is axially movable within the opening 96 relative to the housing body 90. The gear 124 includes a larger cross-sectional size than the opening 96 to limit the extent of axial movement of the first shaft 120 relative to the housing body 90. In one embodiment, when the shaft 120 is biased in a distal direction by the biasing member 70, the shaft 120 is rotationally fixed by square edges near the gear 124 that mate with corresponding square edges within the interior 93 of the housing body 90.

The second shaft 130 is hollow and extends around the exterior of the first shaft 120. The second shaft 130 includes a distal end 131 and a proximal end 132. The distal end 131 includes one or more receptacles 133 on opposing sides that engage with a portion of the structural member 100 that remains within the patient. The proximal end 132 attaches to the housing body 90. The proximal end 132 may include radially-extending projections 134 that fit within gaps 78 formed between tabs 79 in the opening 96 in the housing body 90 (see FIG. 11). The proximal end 132 is attached to the housing body 90 and axially fixed relative to the housing body 90.

The first shaft 120 is axially movable within the second shaft 130. The first shaft 120 is positionable between a first extended position with the distal end 122 of the first shaft 120 extending outward beyond the distal end 131 of the second shaft 130. This positioning exposes the receptacle 123 at the distal end 122 for engaging with the section of the structural member 100 to be removed. The first shaft 120 is also positionable to a second, retracted position with the distal end 122 aligned with or recessed inward from the distal end 131 of the second shaft 130. This causes the one or more receptacles 133 at the distal end 131 of the second shaft 130 to be exposed The instrument 10 may be used in a number of different manners. One manner includes providing a rotational force to a section of the structural element 100 to secure the section within the patient. Using the example of the structural member 100 of FIG. 1, the instrument 10 may be attached to the set screw 100 for attaching it to the head 204 of the anchor 202. Specifically, the receptacle 123 at the distal end 122 of the first shaft 120 engages with the section 100b of the set screw. The instrument 10 is manipulated by the medical practitioner and aligned with the head 204 of the anchor 202. Once aligned, an axial force is applied to the instrument 10 towards the anchor 202. This axial force overcomes the force of the biasing member 70 and causes the first shaft 120 to axially move in the housing body 90. The axial movement causes the gear 124 to engage with the fingers 34 on the drive plate 30. Further, the post 35 on the drive plate 30 may be inserted into the inlet 129 in the distal end 122 of the first shaft 120. A rotational force is then applied to the input mechanism 11. The rotational force causes rotation of the drive gear 20 and cycloidal gear system 13. This rotation is transferred to the first shaft 120 which rotates the set screw into the head 204 of the anchor 202.

The instrument 10 may also be used to remove the excess section of the structural member 100. This process starts with first shaft 120 being in the extended position with the distal end 122 outward beyond the distal end 131 of the housing body 90. The receptacle 123 at the distal end 122 is attached to the section of the structural member 100 to be removed. The section to be removed may extend into the axial bore 126 in the first shaft 120 depending upon its length.

An axial force is applied to the instrument 10 to move the first shaft 120 to the retracted position. This axial movement causes the gear 124 to engage with the fingers 34 on the distal side 37 of the drive plate 30. The movement also causes the distal end 131 of the second shaft 130 to be exposed for attaching to a section of the structural member 100 that remains. In one embodiment, the one or more receptacles 133 at the distal end 131 are configured to attach to an elongated element 201.

A rotational force is applied to the proximal end 24 of the drive gear 20. The rotation of the drive gear 20 causes the second section 22 to rotate within a sweep that is radially offset from the longitudinal axis A.

Rotation of the drive gear 20 is translated to the first gear 60 that is attached to the second section 22, and to the second gear 80 that is attached to the first gear 60. The teeth on the first gear 60 engage with the corresponding teeth on the first annular member 40. The eccentric rotation of the second section 22 of the drive gear 20 causes the first gear 60 to move around the interior surface 45 of the first annular member 40. The first annular member 40 does not rotate because it is fixed to the housing body 90.

The second gear 80 also moves with a sweep around the longitudinal axis A. This eccentric rotation causes the teeth of the second gear 80 to engage with the corresponding teeth of the second annular member 50 around the interior surface 52 of the second annular member 50. This contact also causes the second annular member 50 to rotate with the second gear 80 about the longitudinal axis A of the tool 10. The rotation is possible because the second annular member 50 is not attached to any member that would prevent the rotation.

The first and second gears 60, 80 are axially spaced along the longitudinal axis A for the teeth of the first gear 60 to only engage with the teeth of the first annular member 40, and for the teeth of the second gear 80 to only engage with the teeth of the second annular member 50. The thicknesses of the first and second gears 60, 80 may provide for this limited engagement. Further, the thickness of the spacer 85 positioned between the gears 60, 80 may also provide for this engagement.

The drive plate 30 is attached to the second annular member 50 and therefore rotates with the second annular member 50. The rotation of the drive plate 30 through the fingers 34 causes rotation of the first shaft 120. The first shaft 120 includes the receptacle 123 that is engaged with the section of the structural element 100 to be removed. The force applied to the drive gear 20 is multiplied by the cycloidal gear system 12 and distributed to the first shaft 120 to fracture the section from the remainder of the structural member 100. The attachment of the second shaft 130 with the remaining section of the structural member 100 prevents the "bucking" or "jerking" motion that may occur at the moment the section fractures from the remainder of the structural member 100.

The removed section of the structural member 100 may be captured in the interior bore 126. The instrument 10 may be manipulated to remove the section either through the receptacle 123 or through the outlet 127. Alternatively, the removed section may remain in the interior bore 126 as the instrument 10 is used to remove other sections of other structural members 100. The length of the interior bore 126 may be adequate to hold a number of removed sections.

The drive gear 20 may be configured to receive an input force from a variety of different methods. One type of drive force is provided through a rotational instrument that attaches to the proximal end 24 of the drive gear 20. The shape of the proximal end 24 is configured to engage with the rotational instrument. One type of rotational instrument is the POWEREASE™ Tapper-Driver available from Medtronic, Inc, of Minneapolis, Minn. The drive force may also be provided by the medical practitioner. The proximal end 24 may include a handle (not illustrated) and/or a roughened surface to facilitate contact by the medical practitioner who applies the input rotational force.

The instrument 10 may be used on a variety of different structural members 100. FIG. 1 illustrates the structural member 100 as a set screw for use with an anchor 202 for attaching a rod 201 to a bone 200. One type of set screw with first and second sections 100a, 100b designed for fracture and removal of the first section 100a is SET SCREW, BREAK-OFF available from Medtronic, Inc of Minneapolis, Minn.

Various other structural members 100 may be applicable for use with the instrument 10. Another embodiment features the structural member 100 being a screw with a break away drive head. The screw includes a threaded shaft with a first head section and a second head section. The first head section includes a receptacle for receiving a tool for initially attaching the screw to a bone. The first head section is configured with the second head section for removal after attachment to the bone. One example of a screw with a break away drive head is disclosed in U.S. Patent Application Publication No. 2007/0270859, herein incorporated by reference in its entirety.

The various structural members 100 may include a weakened fracture zone 101 positioned between the first and second sections 100a, 100b. The weakened fracture zone 101 may include a reduced cross-sectional size, a specific cross-sectional shape, a different material composition than the sections 100a, 100b, or various other mechanical aspects. The fracture zone 101 includes a smaller torsional strength than either of the sections 100a, 100b. This results in the structural member 100 fracturing in this zone for separating the first and second sections 100a, 100b.

FIG. 1 illustrates the instrument 10 used for during a vertebral surgical operation. The instrument 10 may also be used in various other surgical settings. Further, the instrument 10 may be used for cutting elongated elements 10 that are not attached to a patient.

Another embodiment of an instrument for removing sections of a structural member is disclosed in co-pending U.S. patent application Ser. No. 12/915,861 which is assigned to the same assignee as the present application.

The instrument 10 may be used during surgical procedures on living patients. The instrument 10 may also be used in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A surgical instrument for applying a rotational force to a structural element comprising:
a housing, an input mechanism, and an output shaft that are each aligned along a longitudinal axis;
the input mechanism including an eccentric shaft with a first section that extends axially on the longitudinal axis and a second section that is radially offset from the longitudinal axis, the input mechanism being rotatable relative to the housing;
the output shaft extends axially on the longitudinal axis and includes a receptacle configured to engage with the structural element, the output shaft being rotatable relative to the housing; and
a cycloidal gear system including:
first and second annular members that are axially spaced along the longitudinal axis, each of the annular members having an opening aligned on the longitudinal axis and teeth that radially extend inward towards a center of the opening, the first annular member has a different number of teeth than the second annular member;
first and second gears that are axially spaced along the longitudinal axis with the first gear aligned to engage with the first annular member and the second gear aligned to engage with the second annular member, each of the gears having teeth that radially extend outward away from the longitudinal axis and engage with the teeth on the respective annular members, the gears being connected to the second section of the eccentric shaft, the first gear having a different number of teeth than the second gear;
one of the annular members being non-rotatably attached to the housing and the other of the annular members being rotatably attached to the housing.

2. The surgical instrument of claim 1, wherein the input mechanism, the output shaft, and the cycloidal gear system are operatively connected for rotation of the input mechanism in a first rotational direction resulting in rotation of the output shaft in the first rotational direction.

3. The surgical instrument of claim 1, wherein the first section of the eccentric shaft extends outward from a first side of the housing and the output shaft extends outward from an opposing second side of the housing.

4. The surgical instrument of claim 3, wherein the second section of the eccentric shaft and the cycloidal gear system are positioned within an interior of the housing.

5. The surgical instrument of claim 1, further comprising a biasing member positioned in the housing between the cycloidal gear system and the output shaft, the biasing member forcing the output shaft away from the cycloidal gear system.

6. The surgical instrument of claim 5, wherein the output shaft is axially movable along the longitudinal axis relative to the housing from a first position with a proximal end of the output shaft spaced away from the cycloidal gear system and a second position with the proximal end spaced in closer proximity to the cycloidal gear system than the first position.

7. The surgical instrument of claim 1, wherein the teeth of the second annular member are positioned a different radial distance from the longitudinal axis than the teeth of the first annular member.

8. The surgical instrument of claim 1, wherein the teeth of the first annular member include a different shape than the teeth of the second annular member.

9. The surgical instrument of claim 1, further comprising a hollow outer shaft that extends over the output shaft, the outer shaft being fixed to the housing to prevent rotation of the outer shaft relative to the housing and to prevent axial movement of the outer shaft relative to the housing.

10. The surgical instrument of claim 1, wherein the output shaft includes a hollow interior and the receptacle is formed in the hollow interior.

11. A surgical instrument for applying a rotational force to a structural element, the surgical instrument having a longitudinal axis, the surgical instrument comprising:
- a drive shaft including a first axial section that extends axially on the longitudinal axis and a second axial section positioned at a distal end of the first axial section and being radially offset from the longitudinal axis;
- a drive member positioned distally from the drive shaft and including a proximal side that faces towards the drive shaft and an opposing distal side, the distal side including fingers that extend axially along the longitudinal axis and are radially spaced outward from the longitudinal axis;
- a first annular member having a central opening that extends around the longitudinal axis and teeth that face radially inward towards the longitudinal axis;
- a first gear attached to the second axial section of the drive shaft and having teeth that extend radially outward away from the longitudinal axis to engage with the teeth of the first annular member;
- a second annular member that is aligned along the longitudinal axis with the first annular member, the second annular member having a central opening that extends around the longitudinal axis and teeth that face radially inward towards the longitudinal axis, the first annular member being attached to the distal side of the drive member, the second annular member including a different number of teeth than the first annular member;
- a second gear attached to the first gear and having teeth that extend radially outward away from the longitudinal axis to engage with the teeth of the second annular member;
- an elongated output member with a first end that engages with the drive member and a second end having a mount configured to engage with the structural element.

12. The surgical instrument of claim 11, further comprising a housing that extends around at least the annular members and the gears, wherein the drive shaft, the drive member, and the output member are rotatable relative to the housing with rotation of the drive shaft in a first rotational direction resulting in rotation of the output member in the same first rotational direction.

13. The instrument of claim 12, wherein a proximal end of the first axial section of the drive shaft is positioned outward from the housing.

14. The instrument of claim 11, further comprising a biasing member that biases the drive member axially away from the second end of the output member.

15. The instrument of claim 14, wherein the output member is axially movable along the longitudinal axis.

16. The instrument of claim 11, further comprising an outer shaft with a hollow interior that extends around the output member.

17. The surgical instrument of claim 11, wherein the second end of the output member includes radially-extending arms that engage with the fingers of the drive member.

18. A surgical instrument for applying a rotational force to a structural element, the surgical instrument having an elongated shape with a longitudinal axis, the surgical instrument comprising:
- an integral input shaft with a first section that extends axially on the longitudinal axis and a second section fixed to the first section and radially offset from the longitudinal axis;
- an output shaft that extends axially on the longitudinal axis and includes a receptacle configured to engage with the structural element;
- first and second annular members that are aligned along the longitudinal axis, each of the annular members having a center opening centered on the longitudinal axis and teeth that radially extend inward toward the longitudinal axis, the first annular member has a different number of teeth than the second annular member;
- first and second gears that are axially spaced along the longitudinal axis, the first and second gears being operatively connected to the second section of the input shaft with the first gear aligned with the first annular member to engage with the first annular member and the second gear aligned with the second annular member to engage with the second annular member.

19. The surgical instrument of claim 18, wherein one of the annular members is non-rotatable about the longitudinal axis and the other of the annular members is rotatable about the longitudinal axis.

20. The surgical instrument of claim 18, wherein the teeth of the first annular member are positioned a different radial distance away from the longitudinal axis than the teeth of the second annular member.

\* \* \* \* \*